United States Patent [19]

Kumoi et al.

[11] Patent Number: 4,845,297
[45] Date of Patent: Jul. 4, 1989

[54] PROCESS FOR PRODUCING POLYAMINES

[75] Inventors: Sadakatsu Kumoi; Keiji Mitarai; Yukihiro Tsutsumi, all of Yamaguchi, Japan

[73] Assignee: Toyo Soda Manufacturing Co., Ltd., Shinnanyo, Japan

[21] Appl. No.: 140,861

[22] Filed: Dec. 30, 1987

Related U.S. Application Data

[63] Continuation of Ser. No. 635,273, Jul. 27, 1984, abandoned.

[30] Foreign Application Priority Data

Aug. 2, 1983 [JP] Japan ............................. 58-140571
Oct. 25, 1983 [JP] Japan ............................. 58-198296

[51] Int. Cl.$^4$ ..................... C07C 85/20; C07C 85/12
[52] U.S. Cl. ............................ 564/487; 564/490; 564/491; 544/402
[58] Field of Search ............... 564/487, 490, 491; 544/402

[56] References Cited

U.S. PATENT DOCUMENTS

| | | | |
|---|---|---|---|
| 3,673,251 | 6/1972 | Frampton et al. | 564/490 |
| 4,146,560 | 3/1979 | Larkin et al. | 564/491 |
| 4,271,088 | 6/1981 | Butte et al. | 260/465.6 |

FOREIGN PATENT DOCUMENTS

| | | |
|---|---|---|
| 0122479 | 6/1944 | Australia . |
| 3248326 | 12/1982 | Fed. Rep. of Germany . |
| 2223236 | 6/1971 | German Democratic Rep. . |
| 2023143 | 12/1979 | United Kingdom . |

*Primary Examiner*—Glennon H. Hollrah
*Attorney, Agent, or Firm*—Oblon, Spivak, McClelland, Maier & Neustadt

[57] ABSTRACT

Process for producing polyamines by a catalytic reduction reaction of a cyanoethylated N-(2-aminoethyl)piperazine and cyanoethylated compounds of polyamines containing 4 or more amino groups in the molecule.

26 Claims, No Drawings

PROCESS FOR PRODUCING POLYAMINES

This application is a continuation of application Ser. No. 06/635,273, filed on July 27, 1984, now abandoned.

BACKGROUND OF THE INVENTION

1. Field of the Invention

The present invention relates to a process for producing polyamines by the catalytic reduction reaction of the cyanoethylated N-(2-aminoethyl)piperazine and the cyanoethylated compounds of the polyamines containing 4 or more amino groups in the molecule.

2. Description of the Prior Art

Generally, polyamines can be produced by a well known process in which the acrylonitriles are added to the polyamines containing the primary and/or secondary amino groups and the resulting cyanoethylated amines are catalytically reduced in the presence of a hydrogenation catalyst under hydrogen atmosphere, to form the polyamines corresponding to the cyanoethylated amines.

In another known process, the catalytic reduction reaction is performed with addition of ammonia to the reaction system to further improve the yield of the polyamines.

SUMMARY OF THE INVENTION

At first, the present inventors investigated the production of polyamines from the cyanoethylated derivatives of N-(2-aminoethyl)piperazine (hereinafter designated as N-AEP) on the basis of those known processes, and it has been found that, if ammonia is not added to the reaction system, a large amount of propylamine is produced as by-product. Therefore, the resultant product mixture contains lowered molecular weight polyamines due to the propylamino groups elimination reactions and a large amount of the heavy amines having a molecular weight greater than 350. As a result, the yield of the target polyamines corresponding to the cyanoethylated polyamines is not satisfactory. In addition to serious economical loss due to the lowered yield of polyamine, the increased amount of by-products of low boiling amines of which propylamine (boiling point : 48° C) is the major product, inevitably introduces disadvantages in the process, such as the removal and recovery of these low boiling amines from the reaction solution which require additional operations and various recovery equipments.

Further, in separating and recovering the used catalyst from the reaction solution, the lowered filterability of the solution due to the poisoned and denatured catalyst is observed, which inevitably leads to increased labor and capital costs. Despite attempts to reduce the costs, by using the recovered catalyst repeatedly, the catalyst is poisoned to almost complete deactivation even with a single use. Thus, waste of the expensive catalyst introduces a tremendously economical loss.

In ordinary processes using ammonia, usually liquid ammonia (boiling point : −33° C.), the processes are complicated due to necessity of troublesome operations and facilities to handle and recover the ammonia, so as to avoid problems caused by ammonia. The addition of ammonia in a small amount shows only a little improvement in the yield of polyamines, and a large amount of ammonia is needed to achieve a satisfactorily high yield of the desired polyamines. In this case, as the partial pressure of ammonia at the reaction temperature can be very high, the apparatus for the reaction should be strong enough for the high pressure, taking into account the high partial pressure of hydrogen which is necessary for the reaction. In addition, a large amount of ammonia to be treated after the reaction inevitably increases the cost for the process. Therefore, the processes described above are not always a profitable one for a commercial production.

Furthermore, the present inventors have investigated the production of the corresponding polyamines from the cyanoethylated polyamines (hereinafter designated as cyanoethylated compounds) which are prepared by adding acrylonitriles to the polyamine compounds of a relatively high molecular weight containing 4 or more amino groups in the molecule. It has been found that the cyanoethylated compounds do not always undergo smooth hydrogenation, if an ordinary known process of hydrogenation is applied. More particularly, the hydrogenation reaction of the nitrile group is largely influenced by the nature of a cyanoethylated compounds, especially differences in the chemical structure and the molecular weight of the precursor amines.

For instance, when the cyanoethylated compounds of the polyamines which contain a number of amino groups in the molecule are hydrogenated without the addition of ammonia, the hydrogenation reaction may proceed halfway or not proceed at all depending on the difference of the catalyst.

When ammonia is added to the reaction solution, the hydrogenation reaction is largely influenced by the nature of the cyanoethylated compounds and by the amount of ammonia added. For example, when an insufficient amount of ammonia is added, the hydrogen absorption reaction may stop midway or not proceed at all. On the other hand, when a large amount of ammonia is used for the reaction to proceed smoothly, similar disadvantages as mentioned hereinbefore are confronted with.

As has been described above, the process for catalytically reducing the cyanoethylated compounds with addition of ammonia is not always accepted as a profitable process with respect to both apparatus and operation.

In this situation, an improved process for the hydrogenation of the cyanoethylated compounds is desired by which the reaction can be carried out, irrespective of the nature of the cyanoethylated compounds, under a relatively low pressure, maintaining an industrially profitable reaction rate, and with simplified reaction operations and easy treatments of the reaction mixtures both during and after the reaction.

The present inventors have devoted their efforts to overcome the difficulties referred to the above and have finally completed this invention. Thus, the present invention provides a new process in which the corresponding polyamines can be produced from the cyanoethylated polyamine compounds containing 4 or more amino groups in their molecules, comprising a catalytic reduction of the cyanoethylated compounds in the presence of an added aliphatic amine containing a primary amino group in the molecule. By employing the aliphatic amine, the process can be performed under a relatively low pressure, maintaining an industrially effective reaction rate while also remarkably suppressing the formation of low boiling by-products.

On the other hand, in the case of a conventional catalytically hydrogenation process of the cyanoethylated N-AEP, low boiling amines will be formed in large amounts, which is unfavorable for the reaction, leading not only to a reduced yield of polyamines but also to a poisoning of the catalyst. In another case of using a large amount of ammonia in the cyanoethylated N-AEP hydrogenation process, the disadvantages of the apparatus and operations are serious, even though the yield may be improved. Therefore, a hydrogenation process for the cyanoethylated compounds has been strongly desired by which useful polyamines can be produced with a high yield under a relatively low pressure using ordinary instruments by simplified reaction operations and easy treatments of the solution both during and after the reaction.

The present inventors, considering above circumstances, intensively investigated the process and found that the catalytic reduction reaction of cyanoethylated N-AEP in the presence of an aliphatic amine containing a primary amino group can afford a high yield of the corresponding polyamines under a relatively low pressure, while the by-production of propylamine can be markedly reduced. This finding has led to the present invention.

In short, the present invention provides a process for producing polyamines from the cyanoethylated compound expressed by the following general formula derived by adding acrylonitrile to N-(2-aminoethyl)piperazine,

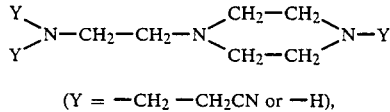

(Y = —CH$_2$—CH$_2$CN or —H), comprising the carrying out of the reduction reaction of the cyanoethylated compound in the presence of a hydrogenation catalyst under the hydrogen atmosphere with addition of an aliphatic amine which contains a primary amino group in the molecule.

Further, this invention provides a process for producing high molecular weight polyamines from the cyanoethylated polyamines derived by adding acrylonitrile to a polyamine compound containing in the molecule at least one primary or secondary amino group and, in total, 4 or more amino groups, comprising performing the catalytic reduction reaction under the hydrogen atmosphere while in the presence of a hydrogenation catalyst with addition of an aliphatic amine containing a primary amino group.

The cyanoethylated compounds are exemplified as follows: (i) monocyanoethylated compounds prepared by the equimolar addition of acrylonitrile to N-AEP such as N-(2-aminoethyl)-N'-(2-cyanoethyl) piperazine and N-(N''-(2-cyanoethyl)aminoethyl)piperazine; (ii) dicyanoethylated compounds prepared by the dimolar addition of acrylonitrile to N-AEP such as N-(N''-(2-cyanoethyl)aminoethyl)-N'-(2-cyanoethyl)piperazine and N-(N''-bis(2-cyanoethyl)aminoethyl)-piperazine, and (iii) tricyanoethylated compound prepared by the trimolar addition of acrylonitrile to N-AEP such as N-(N'''-(bis(2-cyanoethyl)) aminoethyl)-N'-(2-cyanoethyl)piperazine.

The monocyanoethylated, dicyanoethylated and tricyanoethylated compounds mentioned above may be employed alone. However, depending on the use of product polyamines, these raw materials may be used in a mixture of any composition.

On the other hand, the polyamine compounds, containing 4 or more amino groups in a molecule among which at least one is a primary or secondary amino group, are not restricted with respect to their chemical structures, as long as they contain amino groups as specified above. For example, the compounds to be used in this invention as precursor polyamine compounds include those which contain an alkylene chain of 1–12 carbon atoms and 4 or more amino groups such as triethylenetetramine, tetraethylenepentamine, pentaethylenehexamine, tripropyltetramine, tetrapropylenepentamine, pentapropylenehexamine, N,N'-bis(aminopropyl)ethylenediamine, N,N-bis(aminopropyl)ethylenediamine, trihexamethylenetetramine, N,N'-bis(aminopropyl)hexamethylenediamine; those heavy amines which are obtained distillation residue in the process of producing ethyleneamines by the ethylenedichloride method; those amine compounds which are generally called polyalkylenepolyamines; and various mixtures thereof. The combining chains between amino groups are not necessarily alkylene groups, but they may contain ether, thioether, amido and other bindings.

The cyanoethylated compounds of this invention to be used as starting material can be prepared by adding acrylonitrile to the precursor polyamine compounds as described above in detail. Namely, the acrylonitriles are added to the primary or secondary amino groups in the polyamine compounds, to form the cyanoethylated compounds. In general, depending on the number of primary and secondary amino groups in the precursor polyamine compounds and also in the amount of added acrylonitrile, mono- and poly-cyanoethylated compounds which contain one and a plurality of cyanoethyl groups in the molecule are produced. The cyanoethylated compounds of this invention may contain in their molecule one or more cyanoethyl groups and the number of cyanoethyl groups is not particularly restricted. In addition, the cyanoethylated compounds in the form of either a purified single component or a mixture of a plurality of cyanoethylated compounds may be used as raw material for this invention without any substantial difference.

The hydrogenation catalyst to be used in the present invention may include those metal catalysts which are widely used in ordinary catalytic reduction reactions. They include nickel, copper, platinum, ruthenium, palladium, rhodium and iridium. These metals may be employed as carried by diatomeaceous earth, alumina, active clay or active charcoal.

Among the metals mentioned, nickel catalysts are most suited for the reaction of this invention, as considered from the catalyst activity and the economy. Recommended nickel catalysts include Raney nickel, stabilized nickel carried by diatomaceous earth, and nickel catalysts composed mainly of nickel with minor contents of copper, chromium, iron and zinc, and carried by diatomaceous earth. In other words, useful catalysts are composed of nickel as a major component to which other metals are added, or of the mixture of metals which is carried by various carriers. The metals added to nickel are not particularly restricted. The amount of the catalysts used is also not restricted, but it should be determined by considering the productivity connected with the reaction velocity and the yield of polyamines. In general, however, the catalyst is added in an amount of 1–20% by weight against the cyanoethylated compound. Addition of the catalyst in an amount less than 1% by weight is not sufficient to accelerate the reaction velocity, hence not favourable from the standpoint of productivity. More than 20% addition by weight, on the other hand, does not result in a favourable reaction rate nor a satisfactory yield of the polyamines, but only increases the troubles of operation for the removal of the catalyst. The catalyst employed and used according to the process of this invention maintains its high activity even after the use in the reaction and therefore may be removed for recovery from the reaction solution by filtration or decantation for further use in the second and later reactions. This favourably contributes to a reduction in the cost of the catalyst and thus bring a large economical advantage.

The aliphatic amines containing primary amino groups to be used in the present invention include alkylamines expressed by R-$NH_2$ (where R is an alkyl group having 1-8 carbon atoms) and diamines and polyalkylenepolyamines expressed by $NH_2$—R'$+$NH—R''$+_n NH_2$ (where n=0, 1, 2; R' and R'' are alkylene groups having 2-6 carbon atoms; polyalkylenepolyamines include those compounds which contain a cyclic piperazine ring in the molecule).

Typical compounds are listed below.

Alkylamines: methylamine, ethylamine, propylamine, butylamine, cyclohexylamine and 2-ethylhexylamine.
Diamines: ethylenediamine, propanediamine, butanediamine, hexamethylenediamine and cyclohexyldiamine.
Polyalkylenepolyamines: diethylenetriamine, N-(2-aminoethyl) piperazine, triethylenetetramine, dipropylenetriamine, tripropylenetetramine, N-(3-aminopropyl)ethylenediamine.

Alkylamines act not only to suppress the elimination reactions of the cyanoethyl group in the raw material or the aminopropyl group in the reaction products, but also to avoid poisoning of the catalyst. However, if a low boiling amine is employed, such as methyl- or ethylamine, recovery of them from the reaction solution will increase the cost somewhat and therefore the use of a primary alkylamine having a boiling point above 60° C is recommended.

Furthermore, the addition of some amines serves to suppress formation of unfavoured by-products such as propylamine and heavy amines of molecular weight greater than 400 in the cyanoethylated N-AEP hydrogenation reaction, enabling the production of aimed useful polyamines in a high yield under a relatively low pressure of reaction. These useful additives include diamines and polyalkylenepolyamines such as ethylenediamine, propanediamine, propylenediamine, diethylenetriamine, dipropylenetriamine, N-(2-aminoethyl)piperazine, N-aminoethylpropanediamine. When these diamines or polyalkylenepolyamines having relatively low molecular weights are used, they markedly suppress poisoning of the catalyst, and give extremely colorless and high quality polyamines. In addition, they can be readily recovered from the reaction solution by distillation, and therefore exhibit excellent usefulness in the industrial application.

These aliphatic amines are added usually in an amount of 1-50% by weight to the raw material cyanoethylated compounds. If the amount of addition is decreased below 1% by weight, the possible by-production of low boiling amines can be suppressed slightly and the catalyst cannot be maintained at the high activity. And therefore the reaction is retarded and the hydrogenation reaction stops halfway without completion of the reaction. On the other hand, if the amount of added amines exceeds 50% by weight, no further improvement of the reaction can be obtained, but on the contrary, the recovery of a large excess of the aliphatic amines from the reaction solution only increases the cost of recovery without advantage.

Any aliphatic amines, as long as they contain primary amino groups, bring about a number of excellent results in the chemical reaction as well as in operational handiness. In this connection, no restriction is laid on what kind of the aliphatic amine is and in how large an amount it is applied. But the nature and the amount of the aliphatic amines more or less influence the quality and the molecular weight distribution of polyamines formed, and therefore they should be selected for the purpose. For example, in a reaction using an added alkylenediamine, the products are, as well as a polyamine whose structure corresponds to that of the cyanoethylated compound as a starting material, another polyamine containing one more amino group than the above polyamine by the addition reaction of alkylenediamine to the polyamines. In general, industrially produced polyalkylenepolyamines of relatively high molecular weights, such as tetraethylenepentamine and pentaethylenehexamine, are a mixture of polyamines of different chemical structures which may be used for many useful applications such as raw material amine in many fields of industry. Considering these practical usefulness, the method of reaction of this invention provides an excellent process for producing polyamine mixtures having a variety of functions in a flexible way by mere selection of the aliphatic amine to be employed.

The reaction of the present invention is carried out under the hydrogen gas pressure and the range of the pressure is not particularly specified, but usually selected to 1-300 kg/$cm^2$. More preferably, 5-50 kg/$cm^2$ is selected. It is known in hydrogenation reactions of a nitrile group that the pressure of hydrogen has a large effect on the reaction velocity and the yield of aimed amine. In most cases a relatively high pressure, 70 kg/$cm^2$ or above, is applied. However, if an aliphatic amine having primary amino groups in its molecule is added to the reaction system as it is in the present invention, polyamines whose structure correspond to that of the starting cyanoethylated compound, can be manufactured in a high yield and at an efficiently high velocity even if a relatively low pressure of hydrogen, 5-50 kg/$cm^2$, is applied.

In short, the addition of the aliphatic amine permits the reaction to be carried out under a low pressure of hydrogen and makes a profitable condition for the apparatus such as the reaction vessel and compresser. Lowering of the hydrogen pressure leads to the lower reaction velocity and needs a longer time of reaction, but considering the practical productivity the reaction may be conducted at the hydrogen pressure over 5 kg/$cm^2$. The upper limit of the hydrogen pressure is not particularly specified. Since the pressure of hydrogen seriously influences the reaction velocity, it should preferably be selected with the consideration of how to remove the heat evolved as a result of exothermic reactions.

The reaction temperature is also an important factor which has an influence on the reaction speed and the yield of polyamines. The reaction of this invention is usually carried out at a temperature of 80-190° C., preferably 100-170° C. At a temperature below 80° C., the reaction proceeds at a rate too slow to be practically effective. On the other hand, at a temperature above 190° C., the amount of by-products of low boiling amines such as propylamine increases rapidly and also various polyamines having smaller molecular weights than those which correspond to the starting cyanoethylated compounds are produced As a result, the yield of the aimed polyamine decreases.

Any organic solvents and diluents may be added to the hydrogenation reaction system as long as they are inert to nitriles, amines and catalyst. However, no particular advantage can be expected thereby and the addition of a solvent leads to a less effective utilization of the capacity of the vessels.

The process by which materials are supplied to the reaction vessel is not particularly restricted. In one process, cyanoethylated compound, catalyst and primary amines are charged at first, then, hydrogen gas is introduced and the reaction is carried out at a predetermined temperature. In the other process, a catalyst, primary amine and, if necessary, an inert solvent are placed beforehand in a reaction vessel and the reaction is carried out at a predetermined temperature and under a predetermined hydrogen pressure while the starting material cyanoethylated compound is supplied with a peristatic pump.

Usually the reaction of this invention may be carried out in the so-called suspension catalyst system in which the reaction proceeds in a hydrogen atmosphere under agitation in a pressure reactor; or in the fixed bed reaction system in which the favourable effect due to the addition of aliphatic amine containing primary amino group can appear in the same manner. Therefore, the reaction may be carried out by any of the processes.

The solution obtained after the reaction of this invention is treated to remove the catalyst and then distilled to remove a small amount of low boiling amines and the added aliphatic amine. The resulting solution can be treated according to the use of the product polyamine. Thus, if the final product is a mixture of polyamines, the solution may be treated as a whole. When relatively high boiling polyamines which are separable by distillation are desired, the solution should be distilled into fractions to obtain final products. The rectifying distillation may also be utilized to obtain the following polyamines each in the corresponding fraction; tetramine corresponding to the hydrogenation product of monocyanoethylated compound, pentamine corresponding to the hydrogenation product of dicyanoethylated compound, hexamine corresponding to the hydrogenation product of tricyanoethylated compound, and heptamine produced by the side reaction in the polyamine manufacturing derived from the cyanoethylated N-AEP. When a product is manufactured as a mixture of polyamines as mentioned above, a very slightly yellow colored solution obtained by the method of the present invention gives products of a high commercial value.

Notable features of the present invention are seen, for example, in the following. The reaction process of this invention is applied to the production of polyalkylenepolyamines of a relatively high molecular weight. More particularly, a cyanoethylated compounds which contains 3 or more amino groups in the molecule such as cyanoethylated compounds of N-(2-aminoethyl)piperazine and polyamines containing 4 or more amino groups can be treated in the process of this invention. Then, those difficulties such as the intensive poisoning of the catalyst and the remarkable increase in the amount of by-product formation such as of heavy amines and propylamine confronted with in the known arts are improved remarkably by this inventive method. On the other hand, the process of this invention has made it possible to reduce the manufacturing cost by the repeated use of the catalyst, to improve the yield of aimed useful polyamines, and further to discover the mild reaction conditions such as the pressure of hydrogen, and establishes a very useful and profitable industrial process in both the apparatus and operation.

DESCRIPTION OF PREFERRED EMBODIMENT

The present invention will be explained in detail with particular reference to examples, but not restricted thereby.

EXAMPLES 1 –3

In an electromagnetically agitated stainless steel autoclave of a 300 ml capacity, each of the following were charged; 150 g of the cyanoethylated compound of N-(2-aminoethyl)piperazine (N-AEP) appearing in Table 1, 30 g of ethylenediamine and 7.5 g of Raney nickel (in dry base), and the gas phase was replaced by hydrogen. The whole mixture was heated to the reaction temperature and the reaction was carried out at a reaction pressure of 30 kg/cm$^2$. The hydrogenation reaction was conducted at a temperature indicated in Table 1 which was selected according to the species of the cyanoethylated compound of N-AEP. When the absorption of hydrogen ceased, the reaction was continued for additional 20 min. at the same temperature. The reaction solution was cooled. The catalyst used was removed by filtration. Quantitative analysis was made by the gas chromatography on a slightly yellow colored solution obtained. Further, heavy amines having a molecular weight larger than 400 were analyzed by the high performance liquid chromatography, of which the results are shown in Table 1.

TABLE 1

| Example | Raw Material | Reaction Temperature | Reaction Product (g) | | | | | |
|---|---|---|---|---|---|---|---|---|
| | | | Propylamine | Triamine | Tetramine | Pentamine | Hexamine | Heavy amine |
| 1 | Monocyanoethylated Compound | 130° C. | 0.8 | 3.2 | 134 | 12 | 0 | 4.0 |
| 2 | Dicyanoethylated Compound | 140° C. | 0.9 | 0 | 4.8 | 118 | 20 | 10 |
| 3 | Tricyanoethylated | 150° C. | 2.5 | 0 | 4.9 | 28.4 | 67 | 47 |

TABLE 1-continued

| Example | Raw Material Compound | Reaction Temperature | Reaction Product (g) | | | | | |
|---|---|---|---|---|---|---|---|---|
| | | | Propyl-amine | Tri-amine | Tetr-amine | Pent-amine | Hex-amine | Heavy amine |

Triamine: N—(2-aminoethyl)piperazine, N—(3-aminopropyl) piperazine.
Pentamine and tetramine: Polyalkylenepolyamine having 4 or 5 amino groups in the molecule among which 2 are primary amino groups.
Hexamine: Polyalkylenepolyamine having 6 amino groups in the molecule among which 2 or 3 are primary amino groups.
Composition of the raw material cyanoethylated compound (% by weight)
Monocyanoethylated compound: N-AEP 2.1%
Monocyanoethylated compound 97.9%
Dicyanoethylated compound: Monocyanoethylated compound 6.4% Dicyanoethylated compound 92.8% Tricyanoethylated compound 0.8%
Tricyanoethylated compound: Dicyanoethylated compound 14.7% Tricyanoethylated compound 85.3%
Heavy amine: Polyalkylenepolyamines having molecular weight larger than 350

EXAMPLE 4

In the same reaction vessel as that used in Example 1, 150 g of the dicyanoethylated compound of N-AEP, 20 g of 1,3-propane diamine and 6 g of Raney nickel (dry base) were charged, the gaseous phase was replaced by hydrogen and further pressure was applied. While the reaction temperature was being controlled at 135°–140° C., the hydrogenation reaction was conducted at a pressure of 25 kg/cm$^2$. The absorption of hydrogen ceased in an hour after initiation of the reaction, and then the entire mixture was held for 20 min. longer at 140° C. Then, the reaction solution was cooled, the catalyst was removed by filtration, and the slightly yellow colored reaction solution was quantitatively analyzed by the gas chromatography. Heavy amines were analyzed by the high performance liquid chromatography.

The Raney nickel catalyst was separated and recovered from the reaction solution and was used repeatedly 3 more times under the same reaction conditions. Results obtained for the 1st and 3rd runs are expressed in Table 2.

TABLE 2

| | Reaction Products (g) | | | | |
|---|---|---|---|---|---|
| | Propyl-amine | Tetr-amine | Pent-amine | Hex-amine | Heavy amines |
| 1st Reaction | 0.8 | 6.5 | 117.6 | 19.0 | 10.7 |
| 2nd Reaction | 0.9 | 6.8 | 116.7 | 19.4 | 10.9 |

EXAMPLE 5

In the same reaction vessel as used in Example 1 were charged 50 g of dioxane, 7.5 g of Raney nickel (dry base) and 7.5 g of ethylenediamine. The gaseous phase was replaced by hydrogen and pressure was applied. Dicyanoethylated compound of N-AEP in an amount of 150 g was supplied in 2 hours with a peristaltic pump under a reaction pressure of 35 kg/cm$^2$ at 135° C. After the supply was completed, the reaction was continued for an additional hour under the same conditions. Then, the mixture was cooled and the catalyst was removed by filtration. A slightly yellow colored reaction solution obtained was analyzed for its composition by the same methods as used in Example 1. The results obtained were 1.0 g of propylamine, 0.3 g of triamine, 9.4 g of tetramine, 122.1 g of pentamine, 11.2 g of hexamine and 10.0 g of heavy amines.

EXAMPLE 6

In the same reaction vessel as used in Example 1 were placed 150 g of dicyanoethylated compound of N-AEP, 15 g of ethylenediamine and 6 g of 65% nickel (reduced type stabilized nickel) on diatomaceous earth carrier. The gaseous phase was replaced by hydrogen gas and further pressure was applied. The hydrogenation reaction was carried out under a reaction pressure of 31 kg/cm$^2$ at 135° C. The absorption of hydrogen ceased in 1.3 hours after initiation of the reaction and the same condition was maintained for additional 10 min. The reaction solution was cooled and the catalyst was removed by filtration. A slightly yellow colored solution was analyzed for its composition by the same method of analysis as used in Example 1. The results were 0.8 g of propylamine, 0 g of triamine, 7.9 g of tetramine, 119.3 g of pentamine, 16.3 g of hexamine and 10.6 g of heavy amines.

EXAMPLES 7 and 8

In the same reaction vessel as used in Example 1 were charged 150 g of dicyanoethylated compound of N-AEP, 7.5 g of sulfur-resistive nickel catalyst (45 –47% of Ni, 2 –3% of Cr, 3 –4% of Cu, 27–29% of diatomaceous earth and 4–5% of graphite where Ni was in the forms of Ni and NiO) and 15 g of diethylenetriamine in Example 7 and 15 g of N-(2-aminoethyl)piperazine in Example 8. The gaseous phase was replaced by hydrogen gas and further pressure was applied. The hydrogenation reaction was conducted under a reaction pressure of 28 kg/cm$^2$ at 140° C. The absorption of hydrogen ceased in 1.2 hrs. after initiation of the reaction and then the same condition was maintained for additional 15 min. The reaction solution was cooled and the catalyst was removed by filtration. A slightly yellow colored solution was analyzed for the composition by the same method of analysis as used in Example 1. The results obtained in Example 7 were 0.7 g of propylamine, 8.5 g of tetramine, 121.3 g of pentamine, 0.2 g of hexamine, 6.8 g of heptamine and 17.2 g of heavy amines, while in Example 8, 0.7 g of propylamine, 8.3 g of tetramine, 119.8 g of pentamine, 0.3 g of hexamine, 7.2 g of heptamine and 18.2 g of heavy amines.

EXAMPLE 9

In the same reaction vessel as used in Example 1 were charged 150 g of dicyanoethylated compound of N-AEP, 15 g of monoethylamine and 6 g of Raney nickel. The gaseous phase was replaced by hydrogen and further pressure was applied to the hydrogen. The hydrogenation reaction was carried out under a reaction pressure of 35 kg/cm$^2$ at 135° C. The absorption of hydrogen ceased in 1.4 hrs. after initiation of the reaction. The same reaction condition was maintained for 10 min. longer. The reaction solution was cooled and the catalyst was removed by filtration. The reaction solution obtained was analyzed for composition by the same methods of analysis as in Example 1. The results were 1.2 g of propylamine, 0 g of triamine, 14.8 g of tetramine, 123.3 g of pentamine, 0.4 g of hexamine and 12.0 g of heavy amines.

EXAMPLE 10

Preparation of a cyanoethylated compound of triethylenetetramine

Commercial grade triethylenetetramine in an amount of 300 g was placed in a glass-made 4 necked flask of 1 liter capacity which was provided with a stirrer, thermometer, reflux cooler and a dropping funnel. From the dropping funnel, 312 g of acrylonitrile was continually added for one hour, during which time the temperature was maintained at 50° C. After completion of the addition of the acrylonitrile the reaction mixture was further heated to 70° C., and maintained at that temperature for 30 min. under stirring. Gas chromatographic analysis of the reaction mixture showed no presence of unreacted acrylontitrile. Nuclear magnetic resonance spectrum revealed almost quantitative formation of the cyanoethylated compound of triethylenetetramine.

Preparation of polyamines

In an electromagnetically stirred stainless steel autoclave of a 1 liter capacity, 450 g of the cyanoethylated compound of triethylenetetramine, 50 g of ethylenediamine, and 16 g of Raney nickel were charged. The gaseous phase was replaced by hydrogen. The whole was heated to 130° C., and then further pressure was applied to hydrogen. The reaction was carried out under a reaction pressure of 25 kg/cm$^2$ Absorption of a theoretical amount of hydrogen was completed in 4 hrs. after initiation of the reaction, and the mixture was kept at the same temperature for an additional 20 min. The reaction solution was cooled and the catalyst was removed by filtration. The low boiling by-products in the reaction solution were analyzed by the gas chromatography. The results were 9.4 g of propylamine, and 3.3 g of low boiling amines that boil at a temperature range from 50° to 100° C. The reaction solution was further analyzed by the high performance liquid chromatography which revealed the presence of 460 g of polyamines of the mean molecular weight 290. The amine value of the formed polyamines was 1170 mg KOH/g.

EXAMPLE 11

In an electromagnetically stirred stainless steel autoclave of a 1 liter capacity were charged 450 g of cyanoethylated compound of tetraethylenepentamine (a cyanoethylated compound formed by adding 229 g of acrylonitrile to 221 g of tetraethylenepentamine), 67 g of 1,3-propanediamine and 14 g of a 65% nickel (reduced stabilized type) carried by diatomaceous earth, and the gaseous phase was replaced by hydrogen. The whole was heated to 135° C., further pressure was applied to the hydrogen, and the reaction took place under a reaction pressure of 35 kg/cm$^2$. A theoretical amount of hydrogen was completely absorbed in 4 hrs. after initiation of the reaction. The whole mixture was held for 20 min. longer at the same temperature of 135° C. The reaction solution was cooled and the catalyst was removed by filtration. Low boiling by-products in the reaction solution were analyzed by gas chromatography, which revealed the formation of 7.8 g of propylamine, and 1.1 g of low boiling amines having the boiling point between 50° to 100° C. Further analysis of the reaction solution by high performance liquid chromatography showed formation of 465 g of polyamines of the mean molecular weight 420. The amine value of the high boiling point polyamines obtained was 1160 mgKOH/g.

EXAMPLE 12

In the same reaction vessel as in Example 11, a mixture was charged consisting of 450 g of a cyanoethylated compound of pentaethylenehexamine (a cyanoethylated compound formed by adding 211 g of acrylonitrile to 239 g of pentaethylenehexamine), 90 g of diethylenetriamine and 18 g of a sulfur resistive nickel catalyst (composed of 45%–47% Ni, 2% –3% Cr, 3% –4% Cu, 27% –29% diatomaceous earth and 4% –5% graphite where Ni exists in the form of Ni and NiO), and the gaseous phase was replaced by hydrogen gas. The whole was heated to 140° C., pressure was applied to the hydrogen and the reaction was conducted at a reaction pressure of 30 kg/cm$^2$. A theoretical amount of hydrogen was completely absorbed in 4.5 hrs. after initiation of the reaction. The whole mixture was maintained at the same temperature of 140° C. for additional 20 min. The reaction solution was cooled and the catalyst was removed by filtration. The reaction solution was analyzed by the same method as in Example 11. In the reaction products were observed, 8.6 g of propylamine and 0.3 g of low boiling amines having the boiling point ranging from 50° C. to 100° C. Further, 470 g of polyamines having the mean molecular weight of 530, and an amine value of 1100 was obtained.

EXAMPLE 13:

In the same reaction vessel as that used in Example 11, charged were 450 g of a cyanoethylated compound of polyethyleneimine (having a mean molecular weight 1200) (a cyanoethylated compound produced by adding 187 g of acrylonitrile to 263 g of polyethyleneimine), 140 g of ethylenediamine and 18 g of a 65% nickel carried by diatomaceous earth, and the gaseous phase was replaced by hydrogen gas. The whole was heated to 140° C., pressure was applied to the hydrogen, and the reaction was carried out under a reaction pressure of 32 kg/cm$^2$. In 4 hrs. after initiation of the reaction, a theoretical amount of hydrogen was completely absorbed. The same temperature was maintained for an additional 20 min. The reaction solution was cooled and the catalyst was removed by filtration. The reaction solution was analyzed by the same method as used in Example 11. The results were that the solution contained 9.4 g of propylamine, and 3.8 g of low boiling amines having boiling point between 50° C. and 100° C. Furthermore, 472 g of polyamines were obtained having a mean molecular weight of 2,000 and an amine value of 1150.

EXAMPLES 14

In the same reaction vessel as that used in Example 11, charged were 450 g of a cyanoethylated compound of 1,2bis[N-(3-aminopropyl)-3-aminopropoxy]ethane (a cyanoethylated compound formed by adding 171 g of acrylonitrile to 279 g of said etheramine), 60 g of 1,3-propanediamine and 20 g of Raney nickel, and the gaseous phase was replaced by a hydrogen gas. The whole was heated to 135° C., pressure was applied to the hydrogen and the reaction was conducted under a reaction pressure of 45 kg/cm$^2$. A theoretical amount of hydrogen was completely absorbed in 5.5 hrs. after initiation of the reaction. The solution was kept at the same temperature for an additional 20 min. The reaction solution was cooled from which the catalyst was removed by filtration. Then, the solution was analyzed by the same method as in Example 11, which revealed that the solution contained 8.3 g of propylamine and low boiling amines such as 0.4 g of amines having the boiling point between 50° C. and 100° C. Furthermore, 460 g of polyamines were obtained having the mean molecular weight of 500 and the amine value of 830.

COMPARISON EXAMPLE 1

In the same reaction vessel as that used in Example 1, a mixture of 150 g of dicyanoethylated compound of N-AEP, and 7.5 g of Raney nickel (dry base) was charged. The gaseous phase was replaced by hydrogen and a pressure was applied to the hydrogen. The hydrogenation reaction was carried out under a reaction pressure of 30 kg/cm$^2$ at 140° C. The absorption of hydrogen ceased in 7 hrs. after initiation of the reaction. The reaction solution was kept for additional 30 min. at the same temperature. The solution was cooled and the catalyst was removed by filtration. A brown colored reaction solution was quantitatively analyzed using the same method as that in Example 1. The analysis gave 17.9 g of propylamine, 3.1 g of triamine, 22.7 g of tetramine, 84.3 g of pentamine and 21.0 g of heavy amines.

The catalyst separated and recovered in the above reaction was used again under the same reaction condition, but no absorption of hydrogen was observed at all.

COMPARISON EXAMPLE 2

In the same reaction vessel as that used in Example 1, 150 g of dicyanoethylated compound of N-AEP and 7.5 g of Raney nickel (dry base) were charged and the gaseous phase was replaced by hydrogen gas. Liquid ammonia in an amount of 15.0 g was taken in a sample delivery tube, pressure was applied to it and delivered to the reaction vessel. The hydrogenation reaction took place under a reaction pressure of 35 kg/cm$^2$ at 140° C. Absorption of hydrogen ceased completely in 3 hrs. and 40 min. after initiation of the reaction. The reaction was further continued at the same temperature for an additional 30 min. The reaction solution was cooled and the pressure inside was released to purge the ammonia. The yellowish-brown colored reaction solution was quantitatively analyzed for the products by the same method as that used in Example 1. The results were 6.4 g of propylamine, 1.0 g of triamine, 22.0 g of tetramine, 107.3 g of pentamine, 1.5 g of hexamine and 16.3 g of heavy amines.

COMPARISON EXAMPLE 3

In the same reaction vessel as used in Example 1 were charged 150 g of a dicyanoethylated compound of N-AEP and 7.5 g of Raney nickel (dry base) and the gaseous phase was replaced by hydrogen gas. Liquid ammonia in an amount of 5.0 g was taken in a sample delivery tube, given further pressure with hydrogen and introduced in the reaction vessel. The hydrogen reaction took place under a reaction pressure of 35 kg/cm$^2$ at 140° C. The reaction, however, came to stop when 60% of the theoretically estimated amount of hydrogen was absorbed.

COMPARISON EXAMPLE 4

In the same high pressure reactor as used in Example 10, 45of a cyanoethylated compound of triethylenetetramine obtained in the same method as in Example 10 (a cyanoethylated compound produced by adding 230 g of acrylonitrile to 220 g of triethylenetetramine) and 16 g of Raney nickel was charged and the gaseous phase was replaced by hydrogen gas. The reaction took place under a reaction pressure of 35 kg/cm$^2$ after the temperature was elevated to 130° C. In 2 hrs. after initiation of the reaction, an amount of hydrogen corresponding to 10% of the theoretically estimated amount was absorbed, but no further absorption was observed. Even with an elevation of pressure to 70 kg/cm$^2$ and temperature to 150° C., no further progress of the reaction was observed.

COMPARISON EXAMPLE 5

In the same pressure resistive reaction vessel as that used in Example 10, placed were 450 g of a cyanoethylated compound of tetraethylenepentamine (a cyanoethylated compound produced by adding 229 g of acrylonitrile to 221 g of tetraethylenepentamine) and 18 g of 65% nickel (reduced and stabilized nickel) on a diatomaceous earth carrier, and the gaseous phase was replaced by hydrogen gas. Liquid ammonia in an amount of 35 g was taken in a sample delivery tube, applied pressure by hydrogen and introduced to the reaction vessel. The reaction solution was first heated to 135° C., given pressure with a hydrogen gas, and the reaction was carried out under a reaction pressure of 35 kg/cm$^2$. In 5 hrs. after initiation of the reaction the absorbed hydrogen amounted to 60% of the theoretically estimated amount, but no further absorption was observed. With a further increase of temperature to 150° C. and of pressure to 70 kg/cm$^2$, the absorption of hydrogen in an amount of 10% of that estimated theoretically was observed, and then the reaction ceased.

What we claim:

1. A process for producing a polyamine from a cyanoethylated compound, comprising catalytically reducing a compound of the formula

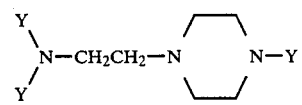

wherein Y is independently a CH$_2$CH$_2$CN group or a hydrogen atom and at least one Y is a CH$_2$CH$_2$CN group, under a hydrogen atmosphere in the presence of a hydrogenation catalyst and an aliphatic amine having at least one primary amino group, wherein the said catalyst is a catalyst composed of nickel as the major component, to obtain as the major product a compound of the formula

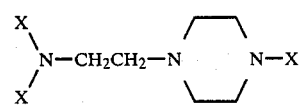

wherein X is a CH$_2$CH$_2$CH$_2$NH$_2$ group or a hydrogen atom, and at least one X is a CH$_2$CH$_2$CH$_2$NH$_2$ group.

2. A process for producing a polyamine from a cyanoethylated compound which is derived by adding acrylonitrile to a polyamine compound containing 4 or more amino groups in the molecule, at least one of which is a primary or secondary amino group, comprising causing a catalytic reduction reaction of said cyanoethylated compound under a hydrogen atmosphere in the presence of a hydrogenation catalyst, wherein the said catalyst is a catalyst composed of nickel as the major component, with addition of an aliphatic amine having two primary amino groups in the molecule.

3. Process according to claim 1 or 2, wherein the hydrogenation catalyst is Raney nickel or nickel carried by diatomaceous earth.

4. Process according to claim 1 or 2, in which the aliphatic amine includes polyalkylenepolyamine expressed by $NH_2-R'-NH-R 41 -_nNH_2$, wherein $n=0, 1, 2$; $R'$ and $R''$ are respectively an alkylene group having $2-6$ carbon atoms.

5. Process according to claim 1 or 2, in which the aliphatic amine is selected from the group consisting of ethylenediamine, propanediamine, diethylenetriamine, dipropylenetriamine, and N(aminopropyl)ethylenediamine.

6. Process according to claim 1 or 2, in which the aliphatic amine is added in an amount ranging from 1 to 50% by weight with respect to the cyanoethylated compound.

7. Process according to claim 1 or 2, in which the reaction is performed under a hydrogen gas pressure ranging from $1-300$ kg/cm$^2$ at a reaction temperature ranging from 80° C. to 190° C.

8. Process according to claim 1 or 2, in which the hydrogenation catalyst is present in an amount of 1% to 20% by weight against the cyanoethylated compound.

9. A process for producing a polyamine from a cyanoethylated compound, comprising catalitically reducing a compound of the formula

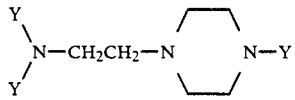

wherein Y is independently $CH_2CH_2CN$ group or a hydrogen atom and at least one Y is a $CH_2CH_2CN$ group, under a hydrogen atmosphere in the presence of a hydrogenation catalyst and an aliphatic amine having at least two primary amino groups, wherein the said catalyst is a catalyst composed of nickel as the major component to obtain as the major product, a compound of the formula

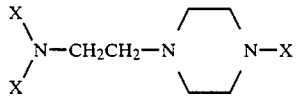

wherein X is a $CH_2CH_2CH_2NH_2$ group or a hydrogen atom, and at least one X is a $CH_2CH_2CH_2NH_2$ group.

10. The process of claim 9, comprising using Raney nickel or nickel on diatomaceous earth as the said hydrogentation catalyst.

11. The process of claim 9, comprising using as the said aliphatic amine a diamine or a polyalkylenepolyamine of the formula $H_2N-R'-(NH-R''\!\!-\!\!)_nNH_2$, wherein $n=0, 1$ or $2$, and $R'$ and $R''$ are each respectively a $C_{2-6}$ alkylene group.

12. The process of claim 9, comprising using as the said amine at least one member selected from the group consisting of ethylenediamine, propanediamine, diethylenetriamine, dipropylenetriamine and N-(aminopropyl) ethylenediamine.

13. The process of claim 9, comprising using the said aliphatic amine in an amount of 1 to 50% by weight relative to the said cyanoethylated compound.

14. The process of claim 9, comprising using a hydrogen pressure of from 1 to 300 kg cm$^{-2}$ and a reaction temperature of 80° to 190° C.

15. The process of claim 9, comprising using the said hydrogenation catalyst in an amount of 1 to 20% by weight relative to the said cyaoethylated compound.

16. The process of claim 1, wherein the said catalyst comprises Raney nickel, stabilized nickel carried by diatomaceous earth, or a nickel catalyst composed mainly of nickel with minor amounts of copper, chromium, iron or zinc and supported on diatomaceous earth.

17. The process of claim 9, wherein the said catalyst comprises Raney nickel stabilized nickel carried by diatomaceous earth, or a nickel catalyst composed mainly of nickel with minor amounts of copper, chromium, iron or zinc and supported on diatomaceous earth.

18. The process of claim 2, wherein the said catalyst comprises Raney nickel, stabilized nickel carried by diatomaceous earth, or a nickel catalyst composed mainly of nickel with minor amounts of copper, chromium, iron or zinc and supported on diatomaceous earth.

19. A process for producing a polyamine from a cyanoethylated compound of the following general formula, which cyanoethylated compound is derived by adding acrylonitrile to N-(2-aminoethyl) piperazine,

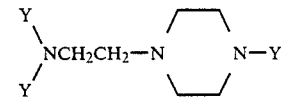

wherein Y is independently a $CH_2CH_2CN$ group or a hydrogen atom and at least one Y is a $CH_2CH_2CN$ group, said process comprising catalytically reducing the said cyanoethylated compound under a hydrogen atmosphere in the presence of a nickel catalyst in the presence of an aliphatic amine having at least two primary amino groups per molecule.

20. A process for producing a polyamine from a cyanoethylated compound, which cyanoethylate compound is obtained by adding acrylonitrile to a polyamine compound containing four or more amino groups per molecule, wherein at least one of the said amino groups is a primary or secondary amino group, said process comprising catalytically reducing the said cyanoethylated compound under a hydrogen atmosphere in the presence of a catalyst composed of nickel as the major component and in the presence of an aliphatic amine having at least two primary amino groups per molecule.

21. The process of claim 19, wherein the said nickel catalyst is Raney nickel or nickel supported on diatomaceous earth.

22. The process of claim 19, comprising using as the said aliphatic amine at least one diamine or polyalkylene polyamine of the formula $H_2N-R'-(NH-R'')_n-NH_2$, wherein n is 0, 1, or 2; an R' and R'' are independently an alkylene group having from 2 to 6 carbon atoms.

23. The process of claim 19, comprising using as the said aliphatic amine at least one member selected from the group consisting of ethylenediamine, propanediamine, diethylenetriamine, dipropylenetriamine, and N-(aminopropyl)ethylenediamine.

24. The process of claim 19, comprising using the said aliphatic amine in an amount ranging from 1 to 50% by weight based on the said cyanoethylated compound.

25. The process of claim 19, comprising using a hydrogen gas pressure of from 1 to 300 kg cm$^{-2}$ and a reaction temperature of from 80° C. to 190° C.

26. The process of claim 19, comprising using a nickel catalyst in an amount of 1% to 20% by weight of nickel based on the cyanoethylated compound.

* * * * *